United States Patent [19]
Aguirre et al.

[11] Patent Number: 5,355,890
[45] Date of Patent: Oct. 18, 1994

[54] PULSE SIGNAL EXTRACTION APPARATUS FOR AN AUTOMATIC BLOOD PRESSURE GAUGE

[75] Inventors: Andres Aguirre, Cambridge, Mass.; James M. Chickering, Newton, N.H.

[73] Assignee: Siemens Medical Electronics, Inc., Danvers, Mass.

[21] Appl. No.: 210,644

[22] Filed: Mar. 18, 1994

Related U.S. Application Data

[63] Continuation of Ser. No. 822,508, Jan. 17, 1992, abandoned.

[51] Int. Cl.$^5$ .............................................. A61B 5/00
[52] U.S. Cl. ............................. 128/680; 128/682; 364/413.03
[58] Field of Search ................. 128/677–686, 128/633, 687, 690; 364/413.03

[56] References Cited

U.S. PATENT DOCUMENTS

| | | | |
|---|---|---|---|
| 4,617,937 | 10/1986 | Peel et al. | 128/682 |
| 4,712,563 | 12/1987 | Link | 128/681 |
| 4,735,213 | 4/1988 | Shirasaki | 128/681 |
| 4,949,389 | 8/1990 | Allebach et al. | 359/557 |
| 4,949,710 | 8/1990 | Dorsett et al. | 128/680 |
| 5,103,831 | 4/1992 | Niwa | 128/687 |
| 5,119,822 | 6/1992 | Niwa | 128/690 |

Primary Examiner—Lee S. Cohen
Assistant Examiner—Robert L. Nasser, Jr.
Attorney, Agent, or Firm—Lawrence C. Edelman

[57] ABSTRACT

An automatic blood pressure gauge generates a signal representing the instantaneous pressure levels in a blood pressure cuff. This pressure signal includes a slowly changing component representing a deflating cuff and a more rapidly changing component representing blood pressure pulses that are mechanically coupled to the cuff. The pressure signal is DC coupled to a microprocessor. The microprocessor filters the pressure signal using a minimum order-statistic filter coupled in cascade with a median order-statistic filter to generate an auxiliary signal having peaks at the starting points of the pulses. This auxiliary signal is used to generate a signal representing the slowly changing component of the pressure signal. The slowly changing component of the pressure signal is subtracted from the pressure signal, leaving only the blood pressure pulse signal. The microprocessor then generates a function representing peaks of the blood pressure pulses versus a corresponding cuff pressure at which they occur. From this function, the microprocessor calculates mean, systolic and diastolic pressures using extrapolation and/or interpolation.

19 Claims, 9 Drawing Sheets

PULSE SIGNAL EXTRACTION APPARATUS FOR AN AUTOMATIC BLOOD PRESSURE GAUGE

CROSS-REFERENCE TO RELATED APPLICATIONS

This is a continuation of Ser. No. 07/822,508 filed Jan. 17, 1992, now abandoned.

This patent application is related to U.S. patent application Ser. No. 07/822,393 of Newell entitled "Pressure Signal Processing Apparatus and Method for an Automatic Blood Pressure Gauge", filed on even date herewith

BACKGROUND OF THE INVENTION

1. Field of the Invention

The present invention is directed to apparatus and a method for automatically measuring the blood pressure of an individual and specifically to an apparatus and a method for separating a pulse signal from the pressure signal produced by an automatic blood pressure gauge.

2. Description of the Prior Art

A conventional automatic blood pressure gauge includes a resilient inflatable cuff and an electric pump. The pump is controlled by a microprocessor to inflate the cuff with a fluid, such as air, to a preset pressure. In addition, this automatic gauge includes a pressure transducer that measures the instantaneous air pressure levels in the cuff. The pressure signal produced by the transducer is used to determine both the instantaneous pressure of the cuff and the blood pressure pulse of the individual. This pressure signal is generally band-pass filtered, digitized and processed by the microprocessor to produce values representing the mean, systolic and diastolic blood pressure measurements of the individual.

In operation, the cuff is affixed to the upper arm area (or other extremity) of the patient and is then inflated to a pressure greater than the suspected systolic pressure, for example, 150 to 200 millimeters of mercury (mmHg). This pressure level collapses the main artery in the arm, effectively stopping any blood flow to the lower arm. Next, the cuff is deflated slowly and the signal provided by the pressure transducer is monitored to detect cuff pressure variations caused by the patient's blood pressure pulse, which is mechanically coupled to the cuff.

In general, the pulse component of the pressure signal has a relatively low amplitude, on the order of one percent of the total signal. A low-level detected blood pressure signal first appears when the cuff pressure is released to a level which allows some blood flow into the collapsed artery. As cuff deflation continues, the blood-pressure pulse signal rises in amplitude as more of the collapsed artery is allowed to expand in response to the pumping action of the heart. At some point, however, the pulse signal reaches a maximum amplitude level and then begins to decrease. This reduction in amplitude occurs as the artery becomes more fully open, the pumped blood flows without significantly expanding the artery, and the degree of mechanical coupling between the cuff and the arm of the patient is reduced.

In many automatic blood pressure measuring systems, the systolic and diastolic pressures are determined based on the cuff pressure at which the blood-pressure pulse signal exhibits maximum amplitude. Such a system is described in U.S. Pat. No. 4,735,213 entitled DEVICE AND METHOD FOR DETERMINING SYSTOLIC BLOOD PRESSURE, which is hereby incorporated by reference for its teaching on automatic blood pressure gauges. In this system, the diastolic blood pressure is determined as the cuff pressure, after the maximum pulse amplitude has been measured, at which the amplitude of the pulse signal is 70% of its maximum value.

Another exemplary system is described in U.S. Pat. No. 4,949,710 entitled METHOD OF ARTIFACT REJECTION FOR NONINVASIVE BLOOD-PRESSURE MEASUREMENT BY PREDICTION AND ADJUSTMENT OF BLOOD-PRESSURE DATA, which is hereby incorporated by reference for its teaching on automatic blood pressure gauges. In this system, the systolic and diastolic blood pressure levels are determined as the respective cuff pressures corresponding to the amplitude of the blood-pressure pulse signal being 60% of the maximum value, prior to reaching the maximum value; and 80% of the maximum value, after reaching the maximum value.

Figure 1A:
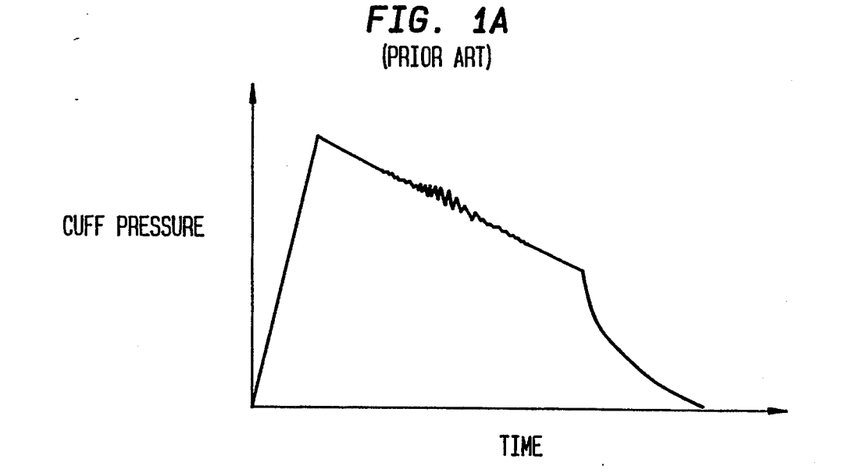
FIGS. 1a through 1c, labeled prior art, are graphs, showing measured pressure variations versus time, which are useful for describing the environment in which the present invention operates.

FIG. 1a is a plot of the pressure signal versus time for a conventional automatic blood pressure gauge. This exemplary signal is generated by the cuff being quickly inflated to a preset initial pressure, greater than the systolic pressure, linearly deflated to a pressure below the diastolic pressure and then quickly deflated the rest of the way. The blood-pressure pulse signal is shown as a waveform superimposed on the linear deflation portion of the pressure curve. For clarity, the relative amplitude of this pulse signal is exaggerated in FIG. 1a.

Figure 1B:
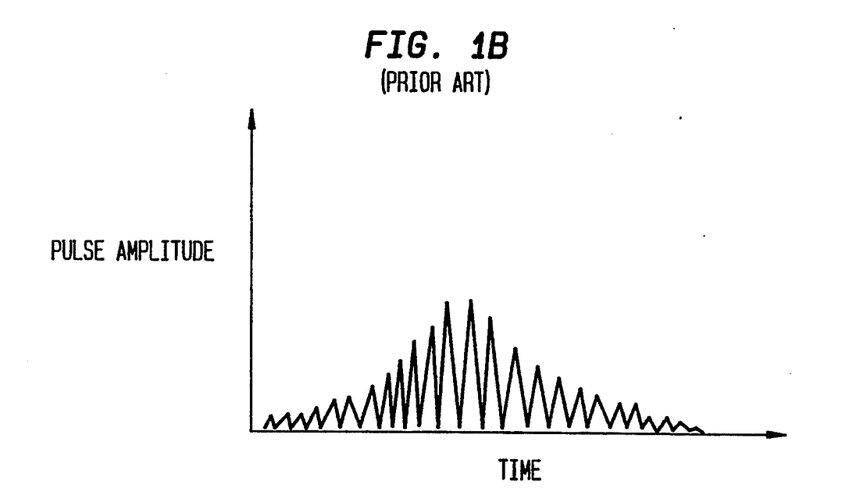
Figure 1C:
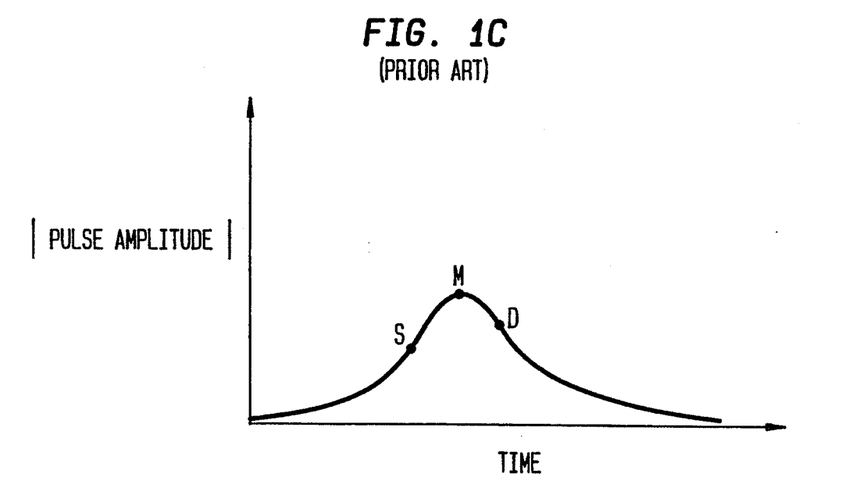

FIG. 1b is a plot of the blood-pressure pulse signal shown in FIG. 1a, separated from the linearly decreasing pressure signal. FIG. 1c is a plot of the peak amplitude of the signal shown in FIG. 1b. As illustrated by FIG. 1c, the amplitude of the pulse signal increases gradually until a time S, at which the linearly decreasing cuff pressure is the same as the systolic pressure of the patient. The amplitude of the pulse signal then increases at a greater rate from time S to time M at which the maximum amplitude is reached. The blood pressure level corresponding to this maximum pulse amplitude is commonly referred to as the mean arterial pressure (MAP). From this maximum amplitude, the pulse signal decreases rapidly to a time D, at which the cuff pressure is the diastolic pressure. The signal amplitude decreases from the point D until the cuff is entirely deflated.

In order to accurately determine the systolic and diastolic pressures of the patient, it is important that the amplitude of the blood pressure pulse signal component of the pressure signal be accurately determined.

In many prior-art automatic blood pressure gauges, including the two that are referred to above, the pressure signal is amplified and band-pass filtered to separate the blood-pressure pulse signal. This signal is then applied to an analog-to-digital converter which has a dynamic range matched to the maximum amplitude of the separated pulse signal.

However, the high-pass component of this band-pass filter may distort the peak-to-peak values of the blood pressure pulse signal by its transient response and its response to the pulse width of the blood pressure signal. The distortion from the high-pass filter can be reduced by having a relatively low high-pass cut-off frequency, but it may then exhibit an unacceptably long transient recovery time which may distort the individual blood-pressure pulses. This is especially true in the case of motion artifacts where large artifact pulsations are introduced to the system. On the other hand, if the high-pass cut off frequency is too high, significant components of the pulse signal may be lost. In addition, if the filter exhibits resonant behavior at any frequency, pulse signals having components which approach this frequency may be distorted by a damped oscillation at the resonant frequency.

SUMMARY OF THE INVENTION

The present invention is embodied in an automatic blood pressure measurement device in which a pressure signal from a deflating cuff is direct current (DC) coupled to circuitry which processes the pressure signal to generate a signal that identifies blood pressure pulses in the pressure signal. The processing circuitry uses the pulse identification signal to extract a signal representing the blood pressure pulses from the DC coupled pressure signal.

According to another aspect of the invention, the processing circuitry includes an order-statistic filter to generate the pulse identification signal.

According to another aspect of the invention, the order-statistic filter includes a minimum filter.

According to yet another aspect of the invention, the order-statistic filter includes a cascade combination of a minimum filter and a median filter.

DETAILED DESCRIPTION OF THE INVENTION

Figure 2:
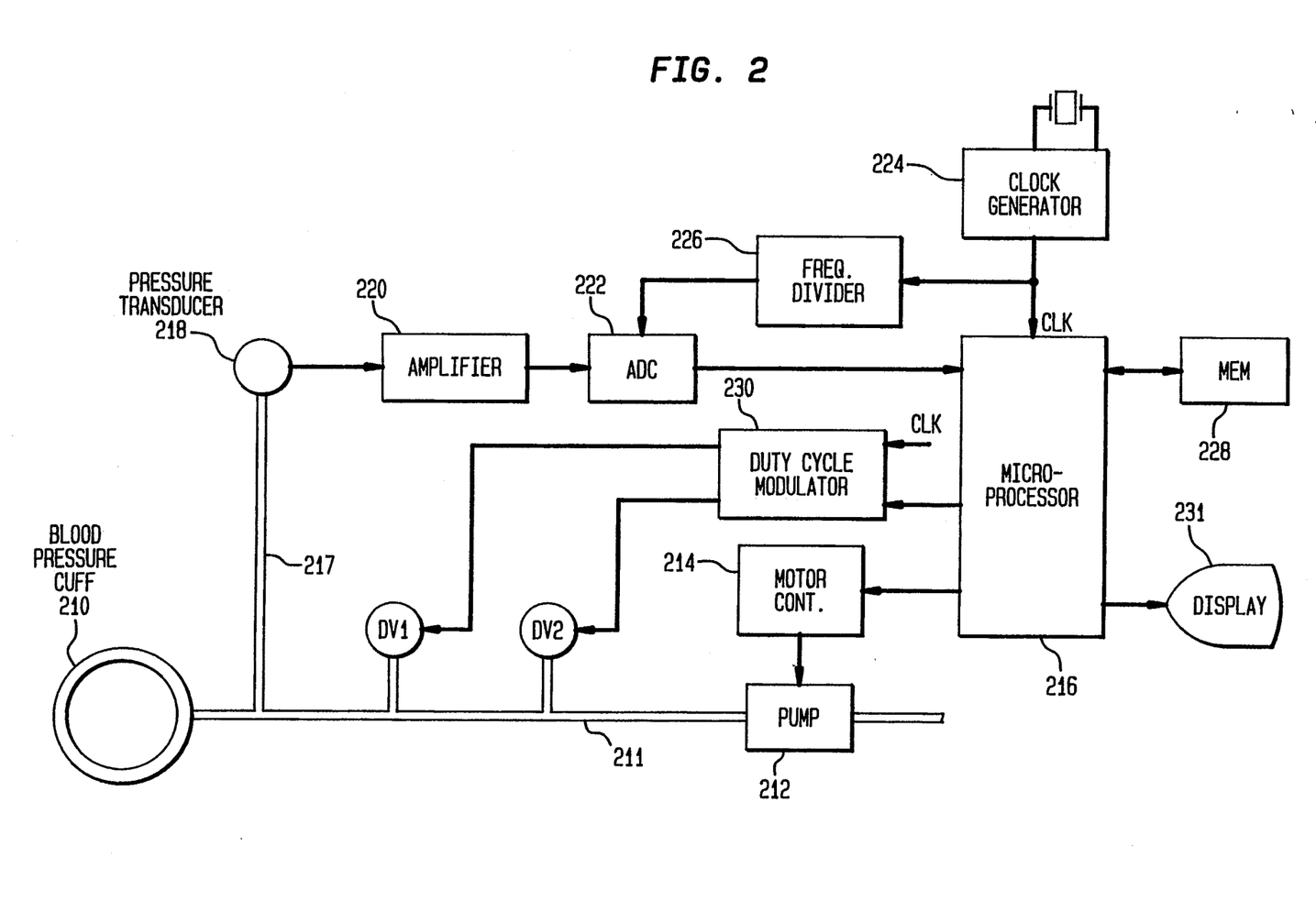
FIG. 2 is a block diagram of an automatic blood pressure measurement system in accordance with the present invention.

FIG. 2 is a block diagram of an exemplary automatic blood pressure gauge according to the present invention. This gauge includes a conventional blood pressure cuff 210 which may be inflated by an electric pump 212 using an air channel 211. The pump motor is turned on and off by a motor controller 214 which is responsive to signals provided by a microprocessor 216. An exemplary pump for use in this embodiment of invention is a diaphragm type driven by a DC motor.

The cuff is deflated using two controlled solenoid valves, DV1 and DV2. When open, the exemplary valve DV1 has a flow rate of 570 standard milliliters per minute (Std ml/min) at 170 mmHg differential pressure, and the exemplary valve DV2 has a flow rate of 1,341 Std ml/min at 20 mmHg differential pressure. These valves may be opened and closed in 1.4 milliseconds (ms) and 6 ms, respectively. In this embodiment of the invention, only one of the valves is open at any given time during normal operation. By controlling the percentage of time within each cycle that the valve is opened and closed, the time-aperture of the valve can be effectively controlled. This time-aperture determines the average rate of airflow through the valve. The selection of the flow rates of the valves DV1 and DV2 allows the microprocessor 216 to control the pressure in the cuff to a relatively high degree of accuracy.

The microprocessor 216 controls the valves DV1 and DV2 using a duty cycle modulator 230. The modulator 230, which is described in greater detail below with reference to FIG. 4, produces a 20.35 Hz signal which controls a selected one of the valves DV1 and DV2. The duty cycle of this signal is controlled to determine the effective aperture of the selected valve, and thus, the rate at which the cuff 210 is deflated.

The microprocessor 216 monitors the air pressure in the cuff using a conventional pressure transducer 218 which is coupled to the air channel 211 via a tube 217. In the exemplary embodiment of the invention, the pressure transducer is of the conventional semiconductor strain gauge type. The signal produced by the transducer 218 is direct-current (DC) coupled to a low-noise instrument quality amplifier 220. The amplifier 220 produces a signal that is DC coupled to an analog to digital converter (ADC) 222.

In this embodiment of the invention, the ADC 222 is a 16-bit sigma-delta type analog to digital converter which produces 50 samples each second. A 16-bit ADC was chosen to provide a relatively wide dynamic range for digitizing the pressure signal. If, for example, the range of the ADC 222 were from +300 mmHg to −50 mmHg, the smallest pressure value that could be represented by the ADC 222 would be 0.008 mmHg.

The exemplary ADC 222 includes a six-pole Gaussian low-pass filter (not shown) which has a pass-band from 0 to 6.5 Hz. Since the effective sampling rate of the ADC 222 is 50 Hz, there is no aliasing of the 20.35 Hz valve switching signal into the band of frequencies (0.5 Hz to 6 Hz) occupied by the blood-pressure pulse signal. Instead, the low-pass filter reduces the amplitude of the valve switching signal component of the pressure signal by more than 20 dB.

The sampled pressure signal data provided by the ADC 222 is monitored by the microprocessor 216 to stop the pump 212 when the desired initial cuff pressure has been obtained, to control the flow through the deflation valves DV1 and DV2, and to determine the new systolic and diastolic blood pressure measurements for the individual.

The blood pressure measurements are presented on a display device 231. To produce these values, the microprocessor 216 operates under the control of a program stored in the memory 228. The memory 228 also contains cells which may be used for storing temporary data values. In the exemplary embodiment of the invention, the program storage portion of the memory 228 is a read-only memory (ROM) while the data storage portion is a random-access memory (RAM).

The microprocessor 216 captures the samples produced by the ADC 222 at the 50 Hz sample rate. These samples are then processed by the microprocessor 216 to further filter any signal components related to the valve switching signal and to extract the pulse signal as described below with reference to the flow-chart diagram of FIG. 6.

The samples provided by the ADC 222 are also processed by the microprocessor 216 in groups of 45 to obtain a noise-reduced cuff pressure signal and its first derivative. The first derivative signal represents the actual rate of change of the cuff pressure. These signals, which have an effective sampling rate of 1.11 Hz, are used to control the deflation valves DV1 and DV2 according to the process shown in FIG. 3.

Figure 3:
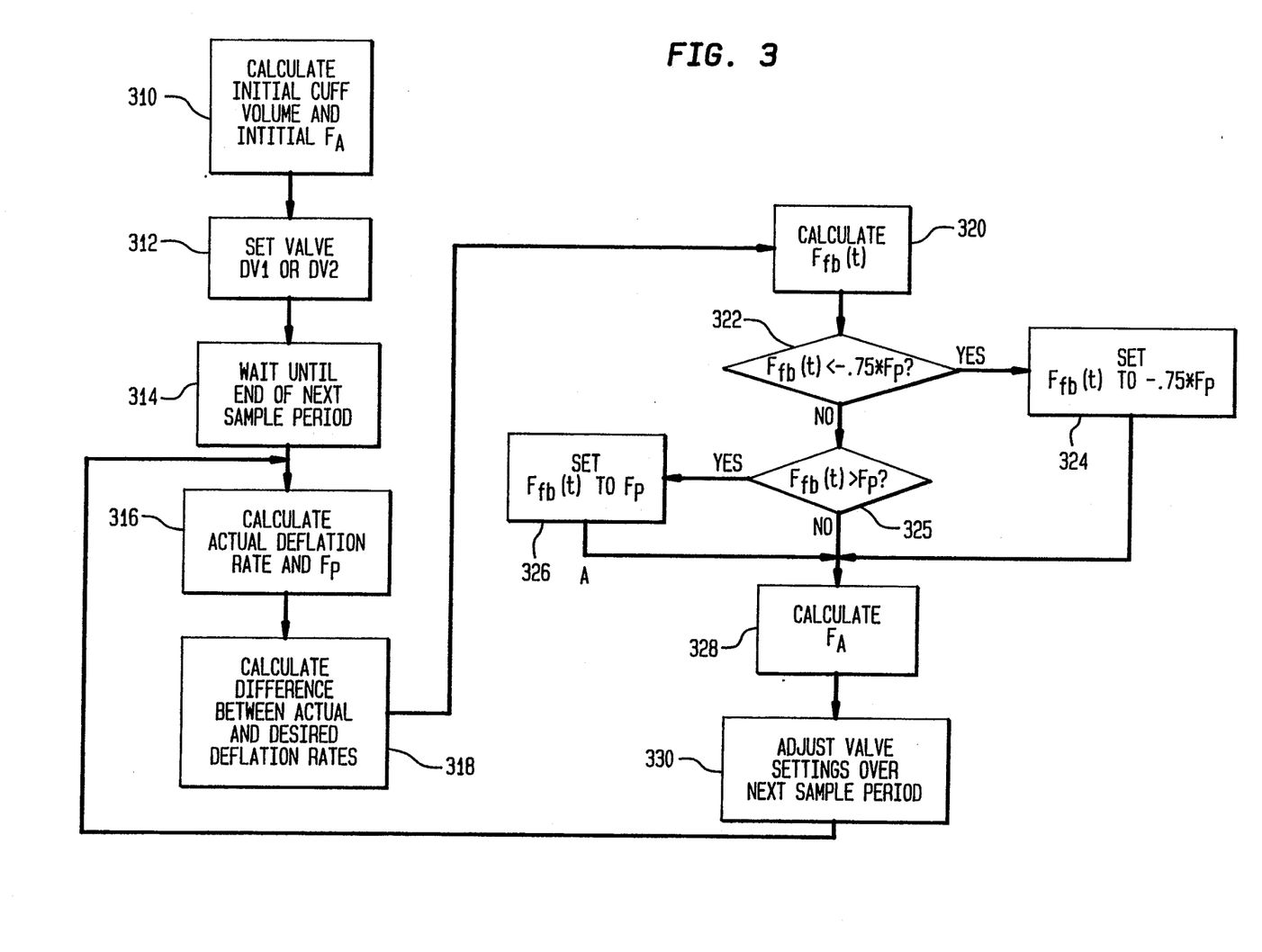
FIGS. 3 and 3a are flow-chart diagrams which are useful for describing the operation of the microprocessor 216.

In the first step of this process, step 310, the initial cuff volume, V, is calculated, one of the deflation valves DV1 or DV2 is selected, and an initial flow setting for the selected valve is calculated. The process used to determine the initial cuff volume is shown in FIG. 3a.

Figure 3A:
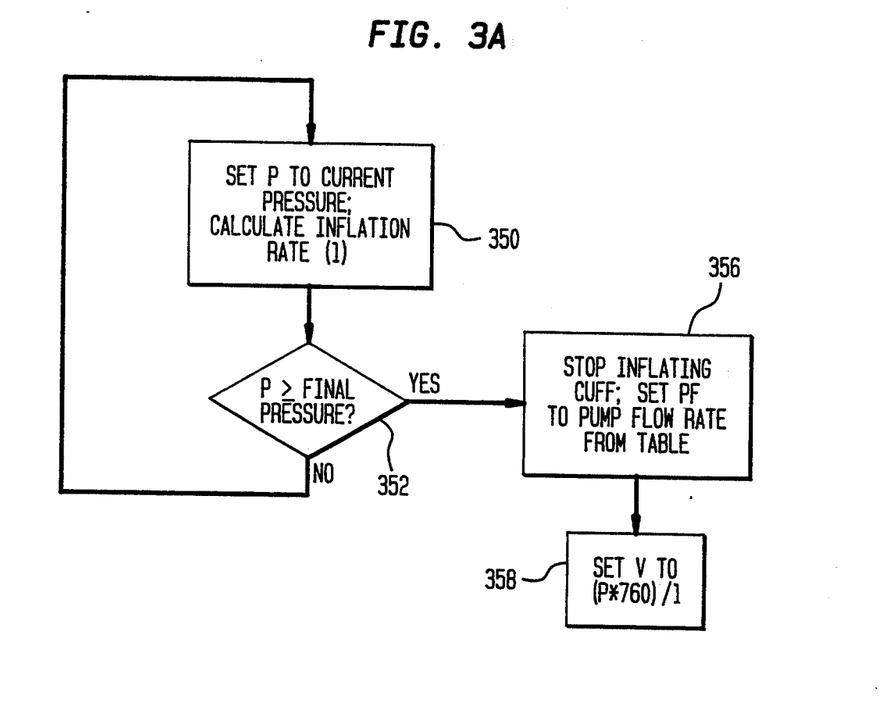

In FIG. 3a at step 350, the microprocessor 216 sets a variable P to the current pressure reading obtained from the pressure transducer 218, and a variable I to the current inflation rate. The inflation rate is a differential pressure value which is obtained by numerically differentiating the pressure signal provided by the transducer 218 over the last 45 sample values. New values of P and I are available at 900 ms intervals as set forth below.

At step 352, the value stored in the variable P is compared to a target final pressure value. If the value in P is less than this target value, then step 350 is executed to continue inflating the cuff, and to continue measuring cuff pressure and inflation rate.

If, at step 352, the value in the variable P is greater than or equal to the target final pressure value, control is transferred to step 356. In this step, the microprocessor 216 signals the motor controller 214 to stop the pump 212 and, thus, stop inflating the cuff. In addition, the microprocessor 216 uses the current pressure value, as stored in the variable P, as an index into a table which provides the current pump flow rate, PF. At step 358, the values PF and I are substituted into the equation (1) to calculate the initial volume, V, of the cuff.

$$V = (PF * 760) / I \quad (1)$$

In this equation PF is the pump flow rate when the cuff pressure has reached its target final pressure value, I is the current inflation rate, and the value 760 represents the pressure of the fluid that is being pumped into the cuff (the flow is specified under standard conditions — 1 atmosphere = 760 mmHg).

The inflation rate is obtained, as set forth above, from the differential signal value generated by the last group of 45 sample values. The value PF is determined from a table of pump flow versus cuff back pressure (BP). An exemplary table is given as Table 1. In this table, the pump flow values are divided by a factor of 50. Thus, the table values are PF/50.

TABLE 1

| PF/50 | BP | PF/50 | BP | PF/50 | BP | PF/50 | BP |
|---|---|---|---|---|---|---|---|
| 58 | 0 | 48 | 67 | 41 | 133 | 32 | 200 |
| 57 | 5 | 48 | 72 | 40 | 138 | 32 | 205 |
| 56 | 10 | 47 | 77 | 39 | 143 | 31 | 210 |
| 55 | 15 | 47 | 82 | 38 | 148 | 31 | 215 |
| 54 | 21 | 46 | 87 | 37 | 154 | 31 | 220 |
| 53 | 26 | 46 | 92 | 37 | 159 | 31 | 225 |
| 52 | 31 | 45 | 97 | 36 | 164 | 30 | 230 |

TABLE 1-continued

| PF/50 | BP | PF/50 | BP | PF/50 | BP | PF/50 | BP |
|---|---|---|---|---|---|---|---|
| 51 | 36 | 45 | 102 | 36 | 167 | 30 | 236 |
| 50 | 41 | 44 | 107 | 35 | 174 | 30 | 241 |
| 50 | 46 | 44 | 113 | 35 | 179 | 30 | 246 |
| 49 | 51 | 43 | 118 | 34 | 184 | 29 | 251 |
| 49 | 56 | 43 | 122 | 34 | 189 | 29 | 256 |
| 48 | 61 | 42 | 128 | 33 | 195 | 29 | 261 |

This table was generated experimentally. To generate a table for a different pump than was used in the exemplary embodiment, the pump is connected to a pressure gauge and to a controllable flow restrictor, such as a needle valve. The output of the needle valve is connected to a flow meter. The flow restrictor is adjusted to generate a given back pressure measurement on the pressure gauge. The flow produced by the pump at that back pressure is measured on the flow meter and recorded. These steps are repeated for all back pressure values to which the pump may be subject in normal operation. To determine the pump flow for a given measured cuff pressure, the table is indexed by the cuff pressure. For pressure values not represented in the table the value of the next lower entry is used.

As an alternative to using this table, a single value may be maintained which represents the nominal flow rate of the pump in a range of back pressures likely to be encountered when the cuff volume is to be determined. This value may be obtained experimentally. For example, the average flow rate of the pump at back-pressures between 150 mmHg and 200 mmHg may be appropriate for adult cuffs.

Once the initial cuff volume has been determined, the initial value of the valve control variable, $F_A$, for the deflation valve DV1 or DV2 is calculated using equations (2) and (3). The value of $F_A$ is a combination of a calculated predictive valve control variable, $F_p$, and a feedback term, $F_{fb}$.

$$F_p = V * R * K_p \quad (2)$$

$$F_A = F_p + F_{fb}(0) \quad (3)$$

In equation (2), R is the desired deflation rate, for example, 6 mmHg/s and $K_p$ is an experimentally determined factor which produces the desired flow rate for different cuff pressures. The value of this factor depends on whether an adult cuff or a neonatal cuff is being used. Exemplary values of $K_p$ for different adult cuff pressure values (ACP) are given below in Table 2. The values in this table are suitable for use with most standard adult cuffs (e.g. arm to thigh). A different set of values (not shown) apply for neonatal cuffs. The cuff pressure in the table is in units of mmHg.

TABLE 2

| $K_p$ | ACP | $K_p$ | ACP | $K_p$ | ACP | $K_p$ | ACP |
|---|---|---|---|---|---|---|---|
| 500 | 0 | 126 | 67 | 64 | 133 | 51 | 200 |
| 500 | 5 | 118 | 72 | 62 | 138 | 51 | 205 |
| 500 | 10 | 108 | 77 | 60 | 143 | 50 | 210 |
| 500 | 15 | 100 | 82 | 59 | 148 | 49 | 215 |
| 450 | 21 | 92 | 87 | 58 | 154 | 49 | 220 |
| 350 | 26 | 84 | 92 | 57 | 159 | 48 | 225 |
| 300 | 31 | 76 | 97 | 56 | 164 | 48 | 230 |
| 250 | 36 | 73 | 102 | 55 | 167 | 47 | 236 |
| 210 | 41 | 69 | 107 | 55 | 174 | 47 | 241 |
| 180 | 46 | 68 | 113 | 54 | 179 | 46 | 246 |
| 160 | 51 | 67 | 118 | 53 | 184 | 45 | 251 |
| 146 | 56 | 66 | 122 | 53 | 189 | 44 | 256 |
| 136 | 61 | 65 | 128 | 52 | 195 | 44 | 261 |

In equation 3, the term $F_{fb}(0)$ is the initial value of a feedback correction term, $F_{fb}(t)$. The algorithm for determining the value of this term while the cuff is being deflated is set forth below. The value of $F_{fb}(0)$ is set to $-0.25*F_p$ for adult cuffs. This term compensates for an initial drop in cuff pressure at the end of the inflation cycle which is due to the release of thermal energy from the compressed air in the cuff.

The value $F_A$ defines the actual valve setting for DV1. If this value is beyond the range of DV1, the value of $F_A$ is scaled for the use of DV2. This value is translated into duty cycles for one of the two valves DV1 and DV2 as described below with reference to FIG. 4.

The next step in the flow-chart diagram shown in FIG. 3, step 314 is to wait until the start of the next update period. In the exemplary embodiment of the invention, the setting for the valve DV1 or DV2 is updated at 900 ms intervals. During this time, the microprocessor is determining the current cuff pressure value from the 45 most recent pressure sample values provided by the ADC 222. As described above, these sample values are processed to eliminate spurious noise spikes. The result of this processing is a noise-reduced cuff pressure signal.

At step 316, this cuff pressure signal is numerically differentiated over the 45 sample interval to produce a signal representing the actual deflation rate. This step may, for example, subtract each pressure sample value from the preceding sample value and average the results to provide a sampled data deflation rate signal for the interval in which the 45 pressure samples were taken. Also at step 316, the predictive valve setting, $F_p$, is determined by applying equation (2) using the most recent cuff pressure sample as the index into Table 2.

The difference, $R_e$, between the actual deflation rate, calculated at step 316, and the desired deflation rate is calculated at step 318. In this embodiment of the invention, the desired deflation rate is 6 mmHg/s.

At step 320, the microprocessor 216 uses the $R_e$ value calculated in step 318 and the equation (4) to compute a feedback term, $F_{fb}(t)$, for the current time interval, t.

$$F_{fb}(t) = (V*R_e*K_g) + F_{fb}(t-1) \quad (4)$$

In the equation (4), $K_g$ is a feedback gain factor. This factor is experimentally determined to produce a desired loop time constant for the feedback loop. In the exemplary embodiment of the invention, this factor has a value of 0.31.

The initial volume factor, V, in the first term of the equation normalizes the transient response of the feedback controller for different cuff volumes. Because of this factor, cuffs having relatively large initial volumes are allowed to have relatively large feedback correction terms while cuffs having relatively small initial volumes are only allowed to have small feedback correction terms. As described above, the initial cuff volume depends on a number of factors such as the size of the patient's arm and how the cuff is wrapped around the arm.

The feedback term $F_{fb}(t)$, as defined by equation (4), is an integrated value since the first term in equation (4), $(V*R_e*K_G)$, is summed with the value of the feedback term from the previous time period, $F_{fb}(t-1)$, to obtain the feedback term for the current time period, $F_{fb}(t)$. In addition, the amplitude of the feedback term is limited to be between $-0.75\ F_p$ and $F_p$ as shown in steps 322 through 326 of FIG. 3. The result of these calculations is a final feedback term, $F_{fb}(t)'$. This term is summed with the predictive valve setting $F_p$ as shown in equation (5) to obtain a new actual valve setting $F_A$.

$$F_A = F_p + F_{fb}(t)' \quad (5)$$

The feedback term is limited to prevent large correction terms from being applied when there is a large transient change in the actual cuff deflation rate. If, for example, the cuff volume is changed because the patient flexed his or her arm, there may be, for a short time interval, a relatively large difference between the actual deflation rate and the desired deflation rate. If the system corrects for this difference in a single step, there would be a continuing error when the flexed muscle is relaxed. This continuing error is caused by the integral nature of the feedback term. In the exemplary embodiment of the invention, the magnitude of these continuing errors is reduced by limiting the amount by which the feedback term may change.

The feedback term $F_{fb}(t)'$ tends to match the actual deflation rate to the desired rate. It compensates for volume changes in the cuff during the deflation process and for valve and pump flow inaccuracies. Since the gain of the feedback loop is relatively low and since the feedback correction term is updated only once every 900 ms, it does not tend to interfere with the blood-pressure pulse signals. This is ensured because the pulse signal frequencies of, for example, 0.5 to 6 Hz, are outside of the range of frequencies that can be tracked by the feedback loop.

If the actual valve setting calculated in step 328 is different from the current valve setting, step 330 changes to the new valve setting gradually over the next 900 ms sample interval. This step is described in greater detail below, with reference to FIG. 5. Following step 330, the program branches back to step 316 to begin the calculations that determine the valve settings for the next interval.

Figure 4:
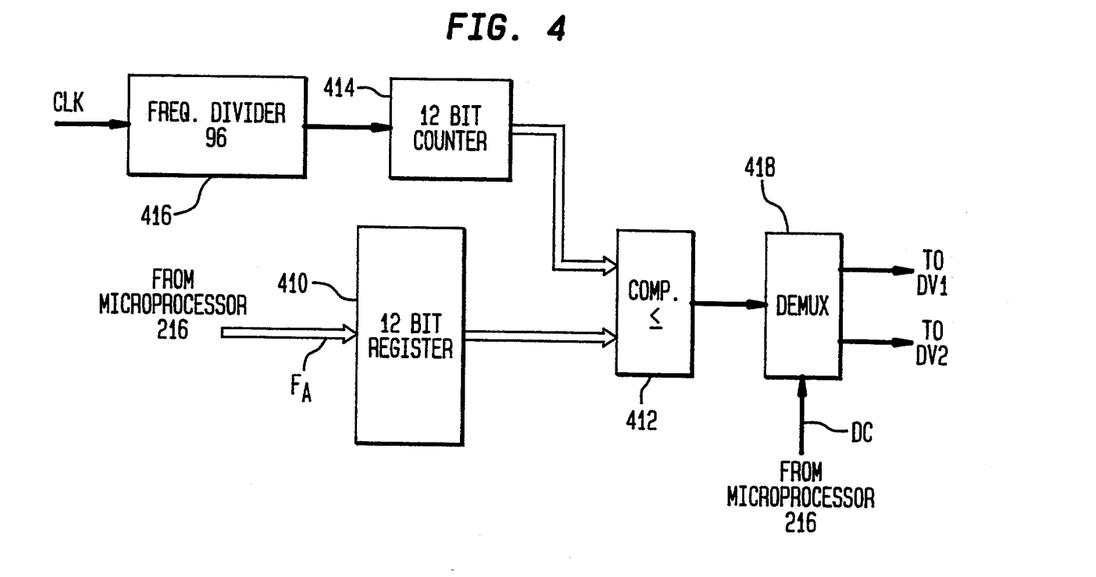
FIG. 4 is a block diagram of circuitry suitable for use as the duty cycle modulator shown in FIG. 2.

FIG. 4 shows exemplary circuitry which may be used as the duty cycle modulator 230 shown in FIG. 2. In this circuitry, a new 12-bit data value, representing the most recently calculated value for $F_A$, is loaded into a register 410 by the microprocessor 216, to change the time-aperture of the currently selected valve DV1 or DV2. As described above, these valves are solenoid valves which may be opened or closed, responsive to a control signal. The valve DV1 or DV2 is open when its control signal is logic-high and closed when its control signal is logic-low.

The control signal for the selected valve is provided by a comparator 412. This comparator compares the value held in the register 410 with a value provided by a 12-bit counter 414. The clock input signal to the counter is the 8 MHz signal CLK divided, in frequency, by a factor of 96 by a frequency divider 416 to produce a clock signal having a frequency of 83.33 KHz. Responsive to this clock signal, the counter cycles through all of its 4,096 values 20.35 times per second.

The comparator 412 is configured so that it produces a logic-high output signal when the value provided by the register 410 is less than or equal to the value provided by the counter 414 and produces a logic-low output signal otherwise. This signal is provided to a demultiplexer 418, which, responsive to a signal DC provided by the microprocessor 216, routes the control signal to either DV1 or DV2.

Figure 5:
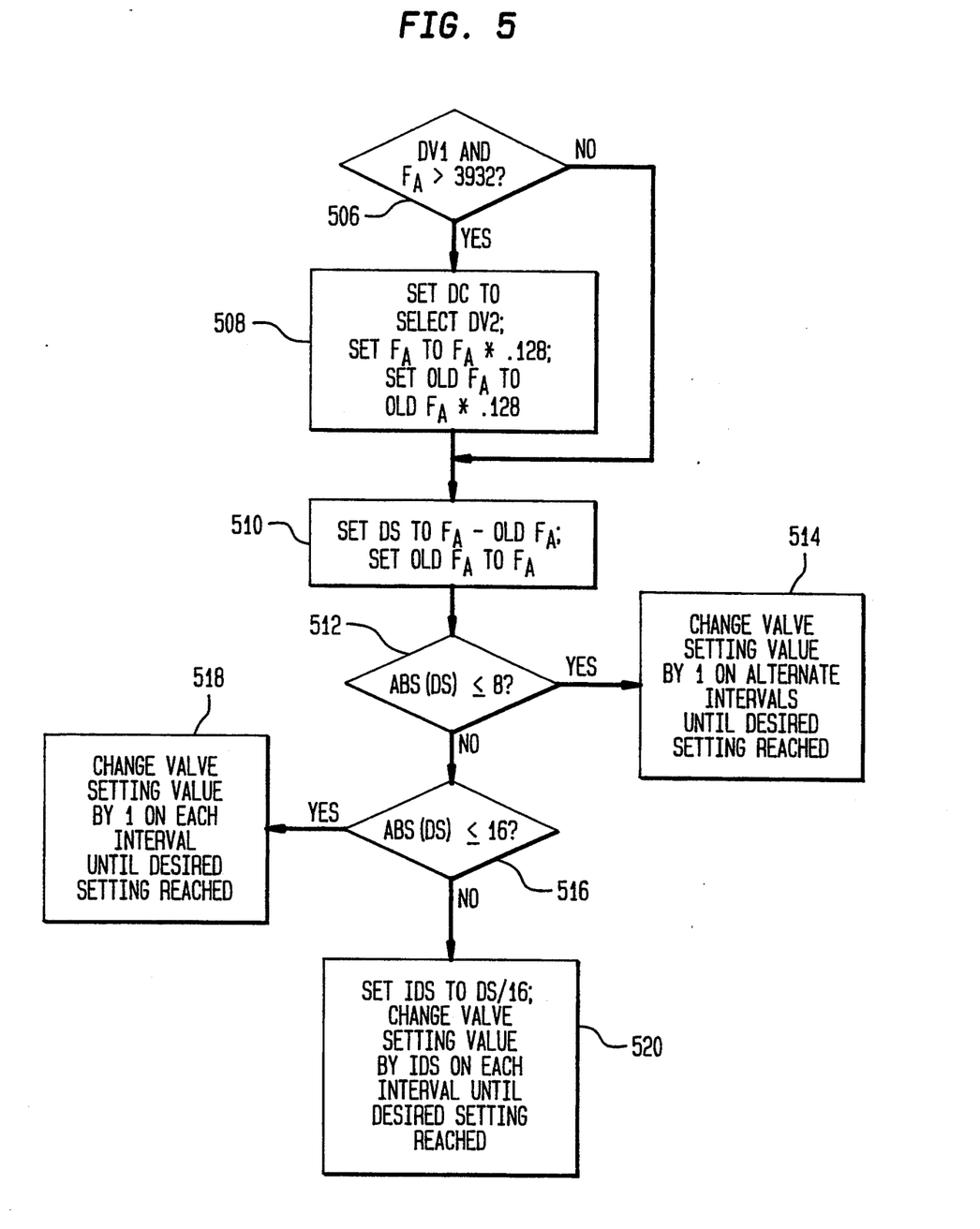
FIG. 5 is a flow-chart diagram which illustrates how the microprocessor shown in FIG. 2 controls the duty cycle modulator shown in FIG. 4.

When the process shown in FIG. 3 selects and adjusts the valve DV1 or DV2 at step 330, it does not make the entire adjustment in one step. Instead, it adjusts the valves gradually over the next 900 ms interval. This is done to prevent artifact pulses which may occur due to sudden changes in flow. FIG. 5 is a flow-chart diagram which illustrates the method by which the microprocessor 216 controls the valves DV1 and DV2 to in response to a new valve setting calculated at step 328.

In the exemplary embodiment of the invention, new values for the valve setting are calculated at 900 ms intervals. The valve settings, however, are each in terms of a duty cycle of a square wave having a period of 49 ms (i.e. 1/20.35 Hz) and the microprocessor can update the value held in the register 410, shown in FIG. 4, at the end of each 49 ms interval. Thus, during each 900 ms interval, the settings for the selected deflation valve DV1 or DV2 can be adjusted as many as 18 times.

The first step in the process which adjusts the settings for these valves, step 506, selects which of the two valves, DV1 or DV2 is to be adjusted. When low flow settings are required to provide the desired deflation rate, such as when a small cuff is deflated at high pressure, valve DV1 is selected. When higher flow settings are required, such as when larger cuffs are deflated at lower pressures, valve DV2 is selected.

When valve DV1 is selected and the value $F_A$ applied to the register 410 is greater than 3,932, step 508 is executed. In this step, the microprocessor 216 changes the signal DC, which is applied to the demultiplexer 418 of FIG. 4, to select valve DV2. At the same time, the microprocessor 216 multiplies the current valve setting value (OLD $F_A$) and the new valve setting value ($F_A$) by 0.128. It then stores the new value for OLD $F_A$ into the register 410. These steps cause an immediate switch to valve DV2 from valve DV1.

Step 510 is executed after step 508, or after step 506 if the comparison in 506 is negative. Step 510 subtracts the new valve setting value, $F_A$, from the current valve setting value, OLD $F_A$, to obtain a value, DS, which indicates the amount by which the current setting must be changed to reach the new setting. Step 512 determines if the absolute value of DS is less than or equal to 8. If so, then at step 514, the microprocessor 216 invokes a procedure which changes the 12 bit number stored in the register 410 of FIG. 4 in unit steps at intervals corresponding to alternate ones of the 20.35 Hz pulses until the desired setting value is reached.

If, at step 512, the absolute value of DS is greater than 8, then step 516 is executed. This step determines if DS is less than or equal to 16. If it is, then step 518 is executed. This step invokes a procedure which changes the 12-bit value stored in the register 410 in unit steps for each pulse of the 20.35 Hz signal until the desired setting value is reached.

If, at step 516, the absolute value of DS is greater than 16, step 520 is executed. This step divides the value DS by 16 to produce a value IDS. Step 520 then invokes a procedure which changes the value in the register 410 by IDS for each pulse of the 20.35 Hz signal until the desired valve setting is reached.

Using the scheme outlined above, the valves DV1 and DV2 provide a wider range of flow rates than would be provided by a single valve. Since the valve setting for DV1 is multiplied by 0.128 before it is applied to the duty cycle modulator as a 12-bit value, the ratio between the smallest and largest possible valve settings is approximately 32,000:1. This wide range of valve settings allows the system to control the linearity of the deflation curve to a high degree of accuracy.

Figure 6:
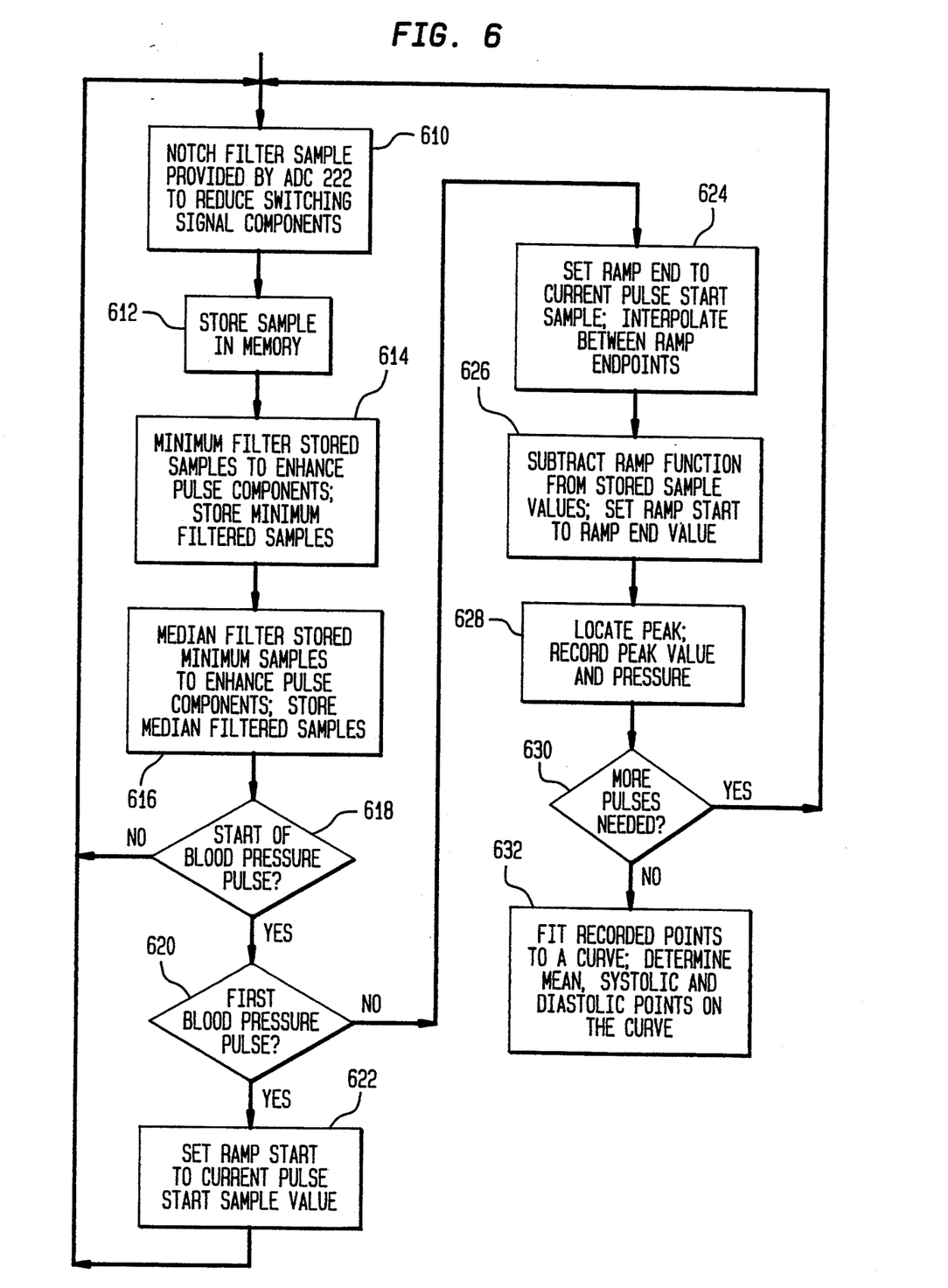
FIG. 6 is a flow-chart diagram which illustrates the process by which the microprocessor shown in FIG. 2 extracts the blood pressure pulse signal from the cuff pressure signal.

FIG. 6 is a flow-chart diagram which illustrates the process by which the microprocessor 216 extracts the pulse signal from the digitized pressure signal provided by the ADC 222. This program processes the sampled-data pressure signal to locate blood pressure pulse signals; extracts these pulse signals and uses the extracted signals to determine mean, systolic and diastolic blood pressure values.

Figure 6A:
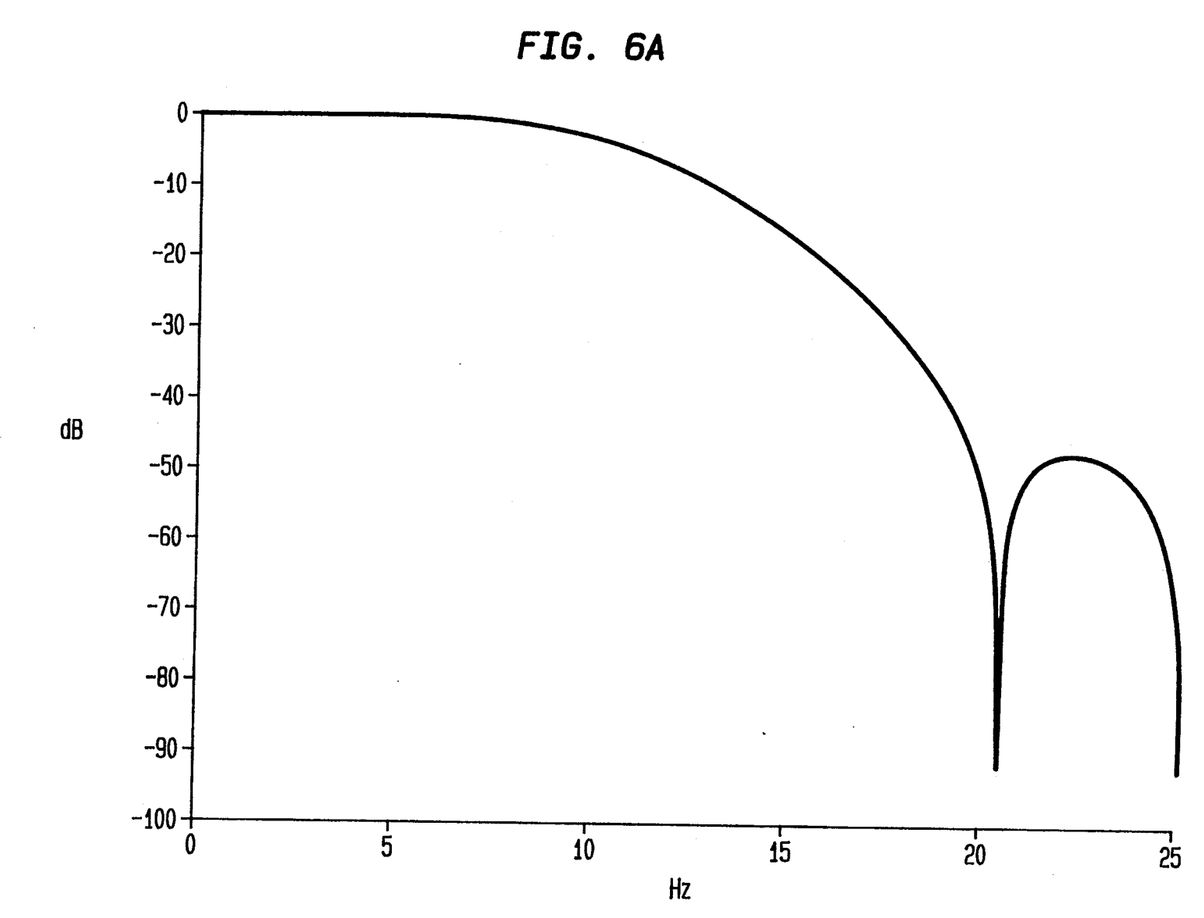
FIG. 6a is a graph of amplitude versus frequency which is useful for describing the effect of a notch filter used in the process of FIG. 6.

At step 610, the microprocessor 216 filters the stored sample values to remove artifacts related to the switching of the solenoid valves DV1 and DV2. The exemplary filter is a third-order Chebychev-2 filter having a notch-type frequency response characteristic which is shown in FIG. 6a. This filter may be readily implemented as a Finite Impulse Response (FIR) or an Infinite Impulse Response (IIR) filter. Techniques for implementing an FIR filter having this frequency response characteristic are described in a paper by J. H. McClellan et al. entitled "A Computer Program For Designing Optimum FIR Linear Phase Digital Filters" IEEE Trans. on Audio and Electroacoustics, Vol. AU-21, NO. 6, December 1973, which is hereby incorporated by reference.

As shown in FIG. 6a, this filter has a zero at 20.35 Hz, the switching frequency of the solenoid valves DV1 and DV2. This filter attenuates artifacts in the pressure signal at the frequency of the valve switching signal by 90 dB relative to the signals in the 0.5 to 6 Hz band of frequencies, occupied by the blood-pressure pulse signals.

Via step 612, the microprocessor 216 continuously stores the notch filtered sampled pressure signal data values in a designated buffer area in the memory 228. In the exemplary embodiment of the invention, the steps following step 612 implement a filter which operates on a moving window of N sample values to produce a new sequence of sample values.

In step 614 and 616, the microprocessor 216 filters the stored sample values to produce an auxiliary sampled data signal which has a one-to-one correspondence to the stored notch-filtered sample values. This auxiliary signal indicates the starting sample numbers of stored notch-filtered pressure sample values which include blood-pressure pulse signal components.

In the exemplary embodiment of the invention, steps 614 and 616 process the notch-filtered sample values through a two-stage order-statistic filter. An order-statistic filter, also known as a rank-order filter, operates on a moving window of sampled data. It effectively sorts the samples in the window by their values and provides as its output, one of the sorted samples. In a minimum order-statistic filter, the smallest of the sorted sample values in the moving window is used as the output signal of the filter. In a maximum filter it is the largest sample value and in a median filter it is the median sample value. See, for example, the article entitled "FIR-Median Hybrid Filters" by Heinonen et al. published in June 1987 in the IEEE Transactions on Acoustics, Speech, and Signal Processing, Vol. ASSP-35, No. 6 for more detailed information about order-statistic filtering.

The particular filter used in the exemplary embodiment of the invention is a cascade combination of a minimum filter and a median filter. The minimum filter (step 614) operates on 21 of the stored, notch-filtered sample values at a time (i.e. N equals 21). When 21 values have been stored, the microprocessor 216, at step 614 averages the ten sample values preceding the middle value of the 21 values (i.e., the intermediate value) and the ten sample values following the middle value to generate two averaged sample values. It then subtracts the smallest of the middle value and the two averaged values from the middle sample value and stores the result as a minimum filtered signal.

The filter implemented by step 614 continues to filter 21 successive sample values in a moving window as each new notch-filtered value is provided by step 610, subtracting the newly determined minimum value from the next new middle (intermediate) value of the stored notch-filtered pressure signal values.

In step 616, the exemplary median filter processes the minimum filtered, sample values in a 41-sample moving window. It averages the first 20 samples in the window and the last 20 samples in the window to generate two averaged values. It then subtracts the median of the two averaged values and the middle value from the middle value of the stored minimum filtered values. This median filtering step proceeds as new minimum sample values are generated. At each successive step, the median of the three values is subtracted from the next new middle value of the stored minimum sample values.

Figure 7A:
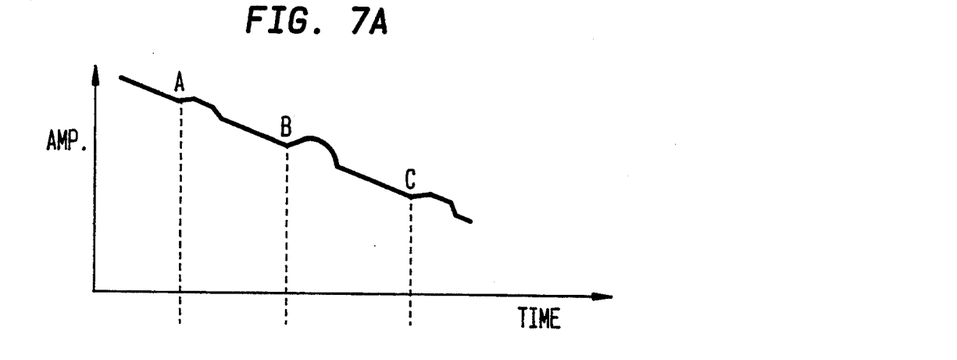
FIGS. 7a through 7d are graphs of amplitude versus time which are useful for describing the process illustrated by FIG. 6.
Figure 7B:
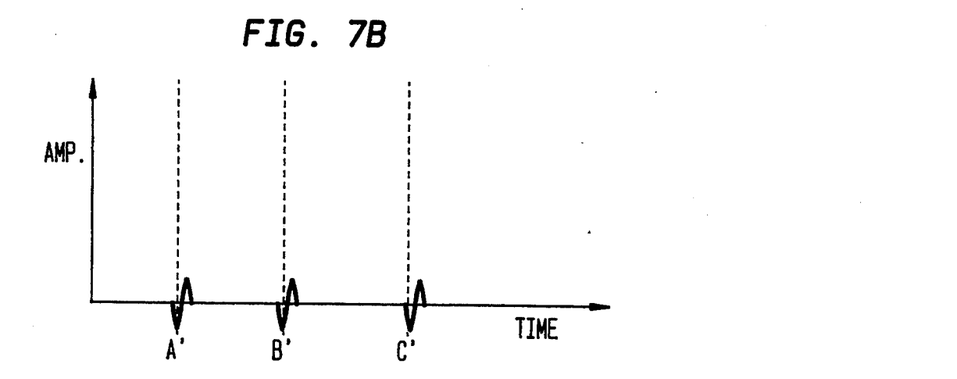

The process performed by steps 614 and 616 is illustrated in FIGS. 7a and 7b. FIG. 7a is a graphical plot of an exemplary notch-filtered pressure signal and FIG. 7b is a graphical plot of the output signal produced by step 616 of the program shown in FIG. 6 after samples including three blood pressure pulses have been processed. As shown in FIG. 7b, the sequence of samples produced by the filtering steps 614 and 616 is a signal (referred to herein as an auxiliary signal) having negative peaks at sample numbers corresponding to the starting point of each blood pressure pulse in the stored notch-filtered pressure signal (points A, B, C in FIG. 7a).

After step 616, the microprocessor 216 processes the notch-filtered samples to extract the blood-pressure pulse signal information. The processing performed by the steps 618 to 630 in FIG. 6 produces samples of the blood-pressure pulse signal, such as those shown in FIG. 7d from samples representing a notch-filtered pressure signal, such as those shown in FIG. 7a. It calculates values of a decreasing ramp signal representing the pressure signal without the blood-pressure pulse signal component FIG. 7c) and then subtracts these calculated values from the notch filtered samples to obtain values representing the blood-pressure pulse signal without the pressure ramp component. The calculated ramp function is a segmented function corresponding to a set of straight lines drawn between the starting points of successive ones of the blood pressure pulses shown in FIG. 1a.

The first step in this process, step 618, examines the successive current samples of the auxiliary signal (FIG. 7b) to find a local minimum value which exceeds a threshold value. Additional checks (for example, minimum value amplitude comparison or cuff pressure check) can be performed to further qualify this local minimum value. This value (e.g. the value at point A' of FIG. 7b) indicates that the corresponding notch-filtered sample value (point A of FIG. 7a) is at the start of a blood-pressure pulse signal. If a pulse is not detected, the process returns to step 610. If a pulse is detected, step 620 determines if this is the first pulse detected by the program. If so, the corresponding notch-filtered pressure sample value is stored, at step 622, as the first sample of the ramp function and as a variable called RAMP START. The process then returns to step 610.

When a subsequent appropriate local minimum is found in the auxiliary signal, step 620 notes that it is not the first detected pulse, and the process jumps to step 624. At step 624, the notch-filtered pressure sample (e.g. point B in FIG. 7a) that corresponds to (e.g., has the same sample number as) the local minimum auxiliary sample (B' of FIG. 7b), is assigned to a variable called RAMP END. Points for the ramp function are then interpolated between the RAMP START and RAMP END variables (e.g. between points A" and B" of FIG. 7c).

Figure 7C:
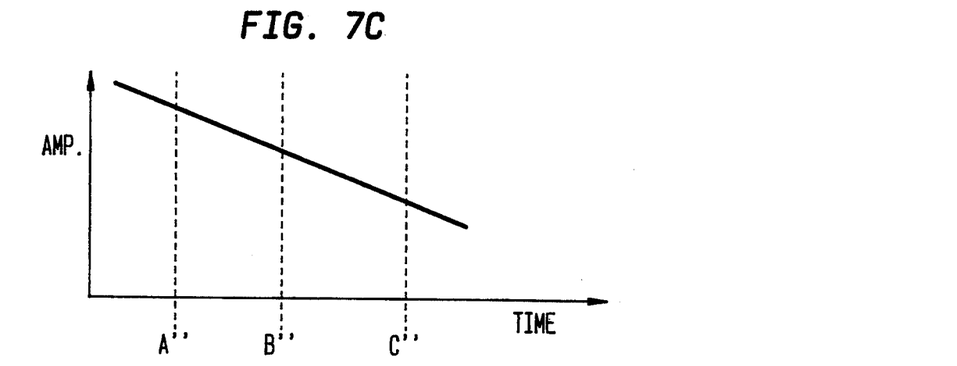

At step 626, microprocessor 216 subtracts the newly calculated points on the ramp function FIG. 7c) from the corresponding notch-filtered pressure samples (FIG. 7a). The resulting sample values (FIG. 7d) represent the blood pressure pulse signal components of the pressure signal to the substantial exclusion of all other components of the pressure signal. The samples calculated in this step contain one blood pressure pulse signal (i.e. the pulse starting at point A of FIG. 7a). Finally, at the end of step 626, the variable RAMP START is set to the value in RAMP END.

Figure 7D:
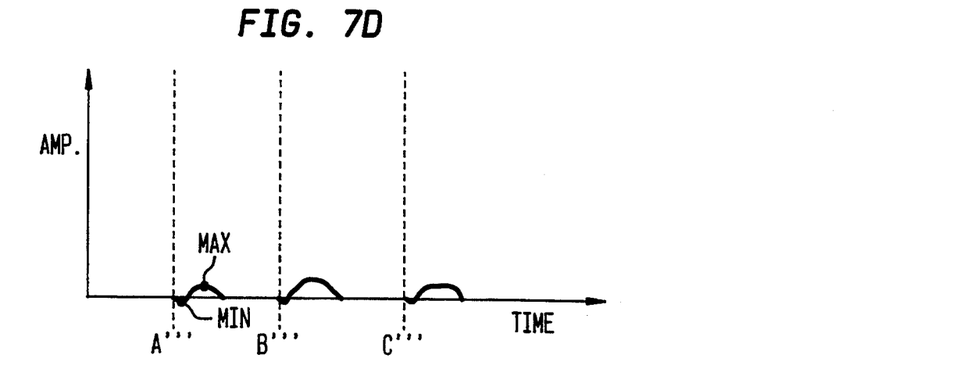

At step 628, microprocessor 216 examines the blood pressure pulse signal components (FIG. 7d) to find the sample number occurring between two adjacent blood pressure pulse start components which have the maximum amplitude value (i.e., γMAX in segment A'''-b''' of FIG. 7d). Next, microprocessor 216 identifies the sample number having a minimum amplitude value which occurs in the blood pressure sample signal just prior to the sample number found having the maximum amplitude value (i.e., γMIN of FIG. 7d). An ordered pair of data is then formed for this blood pressure component information, comprising, the blood pressure pulse peak-to-peak amplitude (i.e., MAX-MIN) and the cuff pressure for that blood pressure pulse component. The cuff pressure is the value of the notch-filtered pressure signal (FIG. 7a) at that sample number which corresponds to the sample number of the MIN amplitude value sample of the blood pressure pulse signal (FIG. 7d).

Step 630 determines if more pulse values are needed by performing a variety of waveshape analysis of the ordered pair data taken so far. If more pulse data is needed, control is returned to step 610 to get the next notch-filtered pressure sample. Otherwise, at step 632, the microprocessor 216 finds a smooth function which defines the recorded peak values in terms of their corresponding cuff pressure values. This function defines a curve which may be identical to that shown in FIG. 1c except that the horizontal axis represents decreasing cuff pressure rather than increasing time. In the exemplary embodiment of the invention, two fourth-order curves are fit to the sample points. One fourth-order curve is fit to the points preceding the one having the largest amplitude (i.e. the MAP point) and the other is fit to the points following the MAP point.

Table 3 shows exemplary pulse amplitude and cuff pressure values developed from a pressure signal similar to that shown in FIG. 1a or FIG. 7a. These points are plotted and fit to a curve in FIG. 8.

TABLE 3

| Peak Number | Amplitude (mmHg) | Cuff Pressure (mmHg) |
|---|---|---|
| 1 | 1.4 | 120 |

TABLE 3-continued

| Peak Number | Amplitude (mmHg) | Cuff Pressure (mmHg) |
|---|---|---|
| 2 | 1.8 | 115 |
| 3 | 2.0 | 110 |
| 4 | 2.1 | 106 |
| 5 | 2.0 | 103 |
| 6 | 1.5 | 95 |
| 7 | 1.3 | 89 |
| 8 | 0.9 | 83 |

The final step in the process illustrated in FIG. 6 finds the systolic and diastolic points using the curve generated at step 632. In accordance with the teachings of Professor Erlanger (see e.g., *Studies in Blood pressure Estimation by Indirect Methods*, Am. J. Physiol. 40:82–125, 1916 and Am. J. Physiol. 55:84–158, 1921) and others well known in the field, the systolic and diastolic pressures can be determined as functions of the pulse amplitude corresponding to the mean arterial pressure (MAP). As set forth above, the MAP is the cuff pressure at which the blood pressure pulse signal exhibits its peak amplitude (i.e. the peak of the curve generated at step 632).

In the exemplary embodiment of the invention, the systolic point is that point on the curve at which the function is at 50% of its maximum value prior to reaching the maximum value and the diastolic point is the point at which the function is at 65% of its maximum value after reaching the maximum value. These amplitude values are translated to systolic and diastolic pressures by locating, interpolating or extrapolating points on the curve that correspond to the determined pulse amplitude values and providing the associated cuff pressure values as the systolic and diastolic pressures. The systolic, mean, and diastolic pressures are then displayed on the display device 231.

Figure 8:
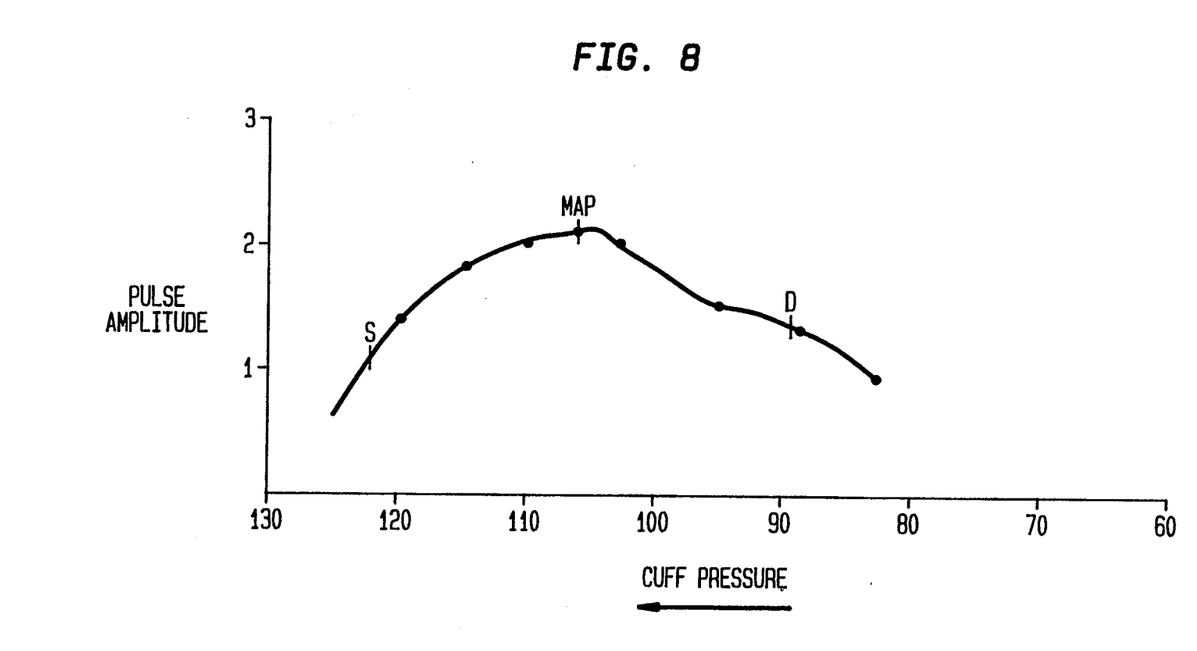
FIG. 8 is a graph of amplitude versus cuff pressure which is useful for describing the process illustrated by FIG. 6.

In the exemplary curve shown in FIG. 8, the systolic point, S, is extrapolated at a pressure level greater than that measured for the first peak and the diastolic pressure is interpolated between the 6th and 7th measured peak pulse amplitude values.

Thus, there has been shown and described a novel blood pressure measurement apparatus which fulfills all the objects and advantages thereof. Many changes, modifications, variations and other uses and applications of the subject invention will, however, become apparent to those skilled in the art after considering this specification and its accompanying drawings which disclose preferred embodiments thereof. For example, although the exemplary embodiment of the invention uses a cascade combination of a minimum order-statistic filter and a median order-statistic filter, it is contemplated that any filter having generally acceptable performance may be implemented without the use of a median filter. In addition, it is contemplated that, if the pressure measurements are to be made as the cuff is inflated, it may be desirable to replace the minimum filter with a maximum order-statistic filter. In fact, in the broadest terms of the invention, it is not even required that the filter be an order-statistic filter, or for that matter, even a digital filter. Furthermore, although this embodiment of the invention uses a linear deflation characteristic, it is contemplated that the invention may be practiced when the blood pressure cuff is deflated according to another curve or when the pulse signal measurements are taken during cuff inflation. If a non-linear deflation or inflation characteristic is used, however, it may be desirable to modify the algorithm which produces the pressure signal without the pulse signal component. The algorithm may be modified, for example, to fit the determined pressure points to a curve which approximates the actual deflation or inflation characteristic. All such changes, modifications, variations and other uses and applications which do not depart from the spirit and scope of the invention are deemed to be covered by the invention which is limited only by the claims which follow.

We claim:

1. A signal processing system suitable for use in an automatic blood pressure gauge which generates at least one blood pressure measurement value and which includes a pressurized cuff and a pressure transducer that generates a cuff pressure signal representing pressure levels in the cuff including blood pressure pulse signal components, the signal processing system comprising:

digitizing means adopted to be direct-current (DC) coupled to receive the cuff pressure signal for developing a sampled data digital cuff pressure signal;

means for filtering the sampled data digital cuff pressure signal to produce an auxiliary signal which identifies samples of the sampled data digital cuff pressure signal that correspond to a start of successive ones of the blood pressure pulse signal components;

pulse signal extraction means, including, a first means responsive to at least two samples of the sampled data digital cuff pressure signal which were identified by the auxiliary signal for generating a base pressure signal by interpolating new pressure signal samples between said at least two samples, which base pressure signal approximates the cuff pressure signal without the blood pressure pulse signal components, and a second means for subtracting the base pressure signal from the sampled data digital cuff pressure signal to produce a separated blood pressure pulse signal; and means for processing the separated blood pressure pulse signal to determine said at least one blood pressure measurement value.

2. A signal processing system according to claim 1, wherein the means for filtering includes an order-statistic filter for enhancement of the blood pressure pulse signal component of the sampled data digital cuff pressure signal.

3. A signal processing system according to claim 2, wherein the cuff pressure signal is generated while the cuff is being deflated and the order-statistic filter includes a minimum filter.

4. A signal processing system according to claim 3, wherein the order-statistic filter includes a median filter coupled in series after the minimum filter.

5. A signal processing system according to claim 3, wherein the minimum filter includes:

means for averaging a first $(N-1)/2$ sequential samples of the sampled data digital cuff pressure signal to generate a first average sample value where N is an integer greater than two;

means for averaging a second $(N-1)/2$ sequential samples of the sampled data digital cuff pressure signal to generate a second average sample value, wherein the second $(N-1)/2$ sequential samples are exclusive of the first $(N-1)/2$ sequential samples and separated therefrom by an intermediate sample; and means for determining the minimum value of the first average sample value, the second average sample value and the intermediate sample value, subtracting that minimum value from said intermediate value to generate a difference value, and for providing successive difference values as a sampled data output signal of the minimum filter.

6. A signal processing system according to claim 5, wherein the order statistic filter further includes a median filter, coupled in cascade after the minimum filter, said median filter comprising:
means for averaging a first (M−1)/2 sequential samples of the output signal of the minimum filter to generate a first minimum average sample value, where M is an integer greater than two;
means for averaging a second (M−1)/2 sequential samples of the output signal of the minimum filter to generate a second minimum average sample value, wherein the second (M−1)/2 sequential samples are exclusive of the first (M−1)/2 sequential samples and are separated therefrom by an intermediate minimum sample; and
means for determining the median value of the first minimum average sample value, the second minimum average sample value and the intermediate minimum sample value subtracting that median sample value from said intermediate minimum sample value to generate a median difference value, and for providing successive median difference values as a sampled data output signal of the median filter.

7. A signal processing system according to claim 1, wherein said first means generates said base pressure signal in a piecewise manner using two successive samples of said sampled data digital cuff pressure signal which were identified by the auxiliary signal.

8. A signal processing system according to claim 7, wherein said first means generates said base pressure signal in a piecewise-linear manner using linear interpolation processing between said two successive samples of said sampled data digital cuff pressure signal.

9. Apparatus suitable for use in an automatic blood pressure gauge which generates at least one blood pressure measurement value and which includes a pressurized cuff and a pressure transducer which generates a pressure signal representing pressure levels in the cuff resulting from blood pressure pulses, the apparatus comprising:
sampling means responsive to said pressure signal for generating a sampled data pressure signal;
order-statistic filtering means for processing the sampled data pressure signal to enhance the blood pressure pulse signal components thereof as compared to the remainder of the pressure signal, and including a series combination of two ranked-order filters, each filter providing a differently ranked sample of said pressure signal applied to its input, as its output;
pulse signal extraction means, coupled to receive an output of the order-statistic filtering means and coupled to receive the sampled data pressure signal, for generating a function representing respective peak amplitudes of successive ones of said blood pressure pulses and respective cuff pressure levels at which the peak amplitudes occur; and
means for calculating said at least one blood pressure measurement value using the determined function.

10. Apparatus according to claim 9, wherein said sampling means includes means for direct current coupling to said pressure transducer and wherein said order-statistic filtering means includes a minimum filter.

11. Apparatus according to claim 10, wherein the order-statistic filtering means includes a median filter coupled in cascade with the minimum filter.

12. Apparatus according to claim 10, wherein the minimum filter includes:
means for averaging a first (N−1)/2 sequential samples of the sampled data pressure signal to generate a first average sample value where N is an integer greater than two;
means for averaging a second (N−1)/2 sequential samples of the sampled data pressure signal to generate a second average sample value, wherein the second (N−1)/2 sequential samples are exclusive of the first (N−1)/2 sequential samples and separated therefrom by an intermediate sample; and
means for determining the minimum value of the first average sample value, the second average sample value and the intermediate sample value, subtracting that minimum value from the intermediate sample value to generate a difference value, and for providing successive difference values as a sampled data output signal of the minimum filter.

13. Apparatus according to claim 11, wherein the order statistic filtering means further includes a median filter coupled in cascade with the minimum filter, said median filter comprising:
means for averaging a first (M−1)/2 sequential samples of the output signal of the minimum filter to generate a first minimum average sample value, where M is an integer greater than two;
means for averaging a second (M−1)/2 sequential samples of the output signal of the minimum filter to generate a second minimum average sample value, wherein the second (M−1)/2 sequential samples are exclusive of the first (M−1)/2 sequential samples and are separated therefrom by an intermediate minimum sample; and
means for determining the median value of the first minimum average sample value, the second minimum average sample value and the intermediate minimum sample value, subtracting that median value from said intermediate minimum sample value to generate a median difference value, and for providing successive median difference values as a sampled data output signal of the order-statistic filter.

14. Apparatus suitable for use in an automatic blood pressure gauge which generates at least one blood pressure measurement value and which includes a pressurized cuff and a pressure transducer which generates a digital sampled data pressure signal representing pressure levels in the cuff resulting from blood pressure pulses, the apparatus comprising:
minimum order-statistic filtering means for processing the pressure signal to produce an output signal in which blood pressure pulse signal components of the sampled data pressure signal are enhanced;
median order-statistic filtering means, coupled in cascade with the minimum order-statistic filtering means for processing the output signal provided thereby to further enhance the blood pressure pulse signal components;
pulse signal extraction means, coupled to receive an output signal of the median order-statistic filtering means for separating the blood pressure pulse signal components from the pressure signal and for generating a function representing peak amplitudes of successive ones of said blood pressure pulse signal components versus cuff pressure levels corresponding to the occurrence of the peak amplitudes, respectively; and means for calculating, from the function, said at least one blood-pressure measurement value.

15. Apparatus according to claim 14, wherein:

the output signal produced by the median order-statistic filtering means identifies samples of the sampled data pressure signal which correspond to first samples of respective groups of samples which include the blood pressure pulse signal components and the pulse signal extraction means includes:

means, responsive to the pressure signal sample values identified by the output signal provided by the median filter means, for generating a base pressure signal which approximates the pressure signal without the blood pressure pulses; and means for subtracting the base pressure signal from the pressure signal to produce said blood-pressure pulse signal components.

16. A signal processing apparatus suitable for use in an automatic patient monitor which generates at least one physiological signal having a relatively slowly varying base component and a more rapidly varying pulsatile information component representative of a physiological condition of the patient being monitored, the signal processing apparatus comprising:

sampling means responsive to said physiological signal for generating a sampled data signal;

order-statistic filtering means for processing the physiological signal to enhance the pulsitile information signal component thereof as compared to the base component, and includes a series combination of two ranked-order filters, each providing a differently ranked sample of said physiological signal applied to its input as its output;

pulse signal extraction means, coupled to receive an output signal of the order-statistic filtering means and coupled to receive the physiological signal, for separating the pulsatile information signal component from the more slowly varying base component of the physiological signal; and means for processing the separated pulse signal component to determine the current condition of the patient represented by said pulsatile information component of the physiological signal.

17. A signal processing system according to claim 16, wherein said sampling means is adapted to be direct current coupled to receive said physiological signal and wherein the order-statistic filtering means includes a minimum filter.

18. A signal processing system according to claim 17, wherein the order-statistic filtering means includes a median filter coupled in series after the minimum filter.

19. A signal processing system according to claim 16, wherein:

direct current coupling means adapted for direct current coupling to said sampling means to receive said physiological signal;

the output signal from said order-statistic filtering means identifies samples of the DC coupled physiological signal which correspond to first samples of respective groups of samples which include the pulsatile information signal component; and the pulse signal extraction means includes:

means, responsive to the physiological signal samples identified by the output signal from said order-statistic filtering means, for generating a base physiological signal which approximates the physiological signal without pulsatile information signal components; and means for subtracting the base physiological signal from the physiological signal to produce said pulsatile information signal component.

* * * * *